United States Patent [19]

Klit

[11] Patent Number: 4,936,153
[45] Date of Patent: Jun. 26, 1990

[54] CORE SAMPLER SYSTEMS

[76] Inventor: Knud K. B. Klit, Gammelby Möllevej 4, DK-6700 Esbjerg, Denmark

[21] Appl. No.: 246,194

[22] Filed: Sep. 19, 1988

[30] Foreign Application Priority Data

Jun. 30, 1986 [DK] Denmark .................... 3097/86
Jun. 30, 1987 [EP] European Pat. Off. ........ 87201235.6

[51] Int. Cl.$^5$ .................... G01N 1/14; G01N 1/08
[52] U.S. Cl. .................. 73/864.33; 73/864.34; 73/864.74; 406/175
[58] Field of Search .......... 73/864.33, 864.34, 864.73, 73/864.74; 209/906; 406/168–175

[56] References Cited

U.S. PATENT DOCUMENTS

| | | | |
|---|---|---|---|
| 1,994,884 | 3/1935 | Chew | 73/864.33 X |
| 3,262,318 | 7/1966 | Decker | 73/864.33 |
| 3,580,084 | 5/1971 | Kramer | 73/864.33 |
| 3,786,682 | 1/1974 | Winter et al. | 73/864.33 X |
| 4,332,301 | 6/1982 | Jonell | 73/864.33 X |

FOREIGN PATENT DOCUMENTS

| | | | |
|---|---|---|---|
| 470807 | 10/1974 | Australia | 73/864.33 |
| 2249493 | 5/1974 | Fed. Rep. of Germany | 73/864.33 |
| 3244514 | 6/1984 | Fed. Rep. of Germany | 73/864.34 |
| 36276 | 11/1970 | Japan | 73/864.33 |
| 391435 | 7/1973 | U.S.S.R. | 73/864.33 |

*Primary Examiner*—Tom Noland
*Attorney, Agent, or Firm*—Antonelli, Terry, Stout & Kraus

[57] ABSTRACT

A cord sampler for sampling impure granular materials a small hole in a wall of the hose connection between a pressure side of a blower and a simple tubular sampling spear, through which hole a weak air flow will be blown out, whereby a correspondingly weak air intake will occur through and open end of the spear, and hereby a considerable improvement of the sampling accuracy is obtained. A similar, but smaller hole may be provided in the suction connection to the spear in order to reduce a vacuum at this place.

6 Claims, 2 Drawing Sheets

CORE SAMPLER SYSTEMS

BACKGROUND OF THE INVENTION

The present invention relates to a core sampler system for taking out samples from loads of granular material and of the type comprising a tubular sampling spear for introduction into selected areas of the material load. Samples are taken, inter alia, for measuring the degree of purity of a charge of material such as grain, seed, beans or other granular material carried by a ship or a truck, e.g. in connection with a truck being placed on a weighbridge, and hereby it is of course crucial that the samples be fully representative of the material. This may contain both relatively heavy and relatively light impurities, and by the introduction of a simple tubular spear the impurities may easily be deplaced in such a manner that they are not received by the spear in exactly the proportions in which they occur in the granular material. Normally there are only a few per cent of impurities in the material, i.e. the samples should ideally be taken with an extreme accuracy to ensure a representative distibution of the impurities in the samples.

It has been found long ago that samples taken by a simple introduction of a tubular sampling spear will normally be very far from being representative with respect to the impurities in the material, and great efforts have been made to improve this circumstance. Thus, it has been endeavored to achieve a certain improvement by carrying out a suction on the tubular sampling, but it has been found, however, that an associated "vacuum cleaner effect" at the insertion end of the spear has caused a suction intake of a disproportionately large amount of impurities from the surroundings of the spear tip, such that the sample result is still not fully representative. The result may even be still more inaccurate, particularly with materials having relatively large particles, e.g. beans and peas.

The most accurate results so far have been obtained by using a tubular sampling spear consisting of an inner suction pipe and a surrounding pipe for supply of pressurized air, the insertion end of this spear being embodied as a short, exteriorly tapering pipe portion, which communicates axially with the mouth of the central suction pipe through an inner ring slot area wherefrom air is conveyed into the inner mouth of the suction pipe from the surrounding pressurized air pipe. The spear is connected in a closed air circulation system in which the pressure side of the blower is connected directly to the pressurized air supply of the spear, while the suction pipe of the spear, i.e. the outlet pipe for air and grain is connected to the suction side of the blower through a grain separator. It is aimed at that the static air pressure in the ring nozzle area corresponds to the ambient pressure or is very close to this, such that adjacent the ring slot no considerable over- or subpressure will occur, which might be transmitted to the material inside and outside the end of the spear. By this system strongly improved results have been obtained, probably because the material is conveyed away from the spear end without any associated "vacuum cleaner effect" and without the material in compact form being able to penetrate into the spear further than through the short, distance from the tip to the ring nozzle area. Thus, hereby no long "plug" will be formed in the pipe, which through friction against the inner sides of the pipe might cause a noticable pressure against the material, which, by the insertion of the spear, is about to be introduced into the spear pipe, and it is presumed that by sample taking with a simple pipe spear with associated closable slots it is such a pressure build-up in front of the spear tip which, by the movement of the spear and by the opening and closing of the said closeable slots thereof, contributes to the considerable inaccuracy of the sample taking.

The invention relates to a sampling system of the abovementioned air circulation type, and its purpose is to provide such a modification of this type of system that a further improvement of the sample accuracy is obtainable, the previously obtained accuracy being relatively good, but not at all satisfactory, particularly when the impurities consist of seed weeds, sand, or soil particles. The invention is based on the consideration that a very weak suction effect could be established advantageously at the spear end, which would facilitate the material passage through the short "plug portion" between the outer spear tip and the ring slot area, such that a pressure build-up in front of the spear tip may be further reduced without any considerable or harmful vacuum cleaner effect.

According to the invention such a weak suction effect is not provided through any changed dimensioning of the system, but through the very simple measure of a small hole being provided in the wall of the air conduit on the pressure side of the blower in the closed system, preferably close to the the concerned junction between the sampling spear and an air supply hose connected thereto, and preferably a hole having an area of the magnitude 1/10 of the diameter of the suction pipe. A certain amount of air will be pressed out through this hole during the operation of the system, and as the system is otherwise closed, this air outlet must result in a corresponding suction intake effect in such a part of the system where this is possible, i.e. at the spear end as being open to the surroundings such that the desired weak suction effect is brought about in a well-defined manner just at this place. A large number of experiments have proven that with the system according to the invention it is possible to obtain a highly improved accuracy of the sample taking, even though it must be admitted that a precise explanation of this fact be given, The optimal size of the hole will depend on the basic parameters of the air circulation system, and it can be mentioned that the hole should be of a slightly increasing size, the larger the conduit or hose connection between the blower and the spear is. Under circumstances as explained below it may even be desirable to provide a corresponding, but smaller hole in a wall portion of the suction side of the system.

BRIEF DESCRIPTION OF THE DRAWINGS

In the following the invention is described in more detail with reference to the accompanying drawing wherein.

DETAILED DESCRIPTION

Figure 1:
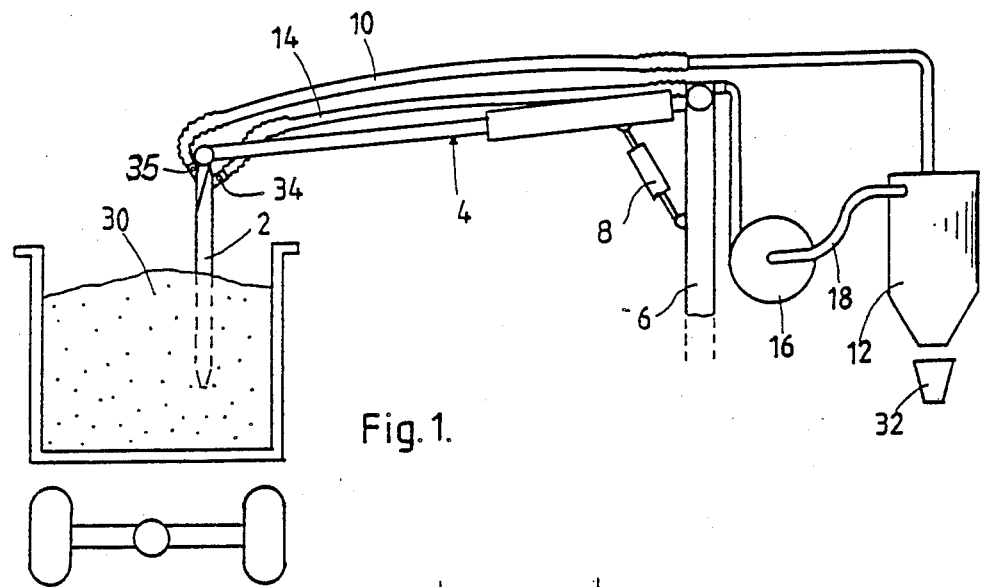
FIG. 1 is a schematic view of a sampling system according to the invention.

The system shown comprises a sampling spear 2 which is suspended in a longitudinally variable outrigger arm generally designated by the reference numeral 4 on a fixed, rotatable column 6, with the arm 4 being swingable by a cylinder 8. The upper end of the spear 2 is connected to a first conduit 10 which leads to a material separator 12, and to a second conduit 14, which leads to the pressure side of a blower 16, the suction side of which being connected to the separator through a suction hose 18.

Figure 2:
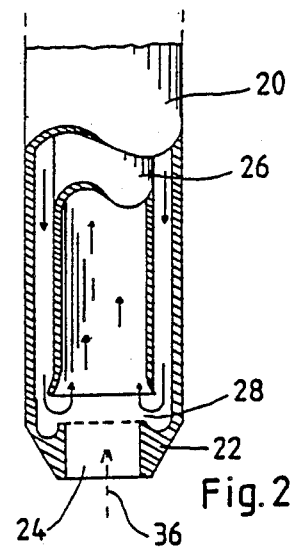
FIG. 2 is a detailed sectional view of the outer end of an associated sampling spear and also shows a view of part of the upper portion of the associated sampling spear in another embodiment of the invention.

As shown in FIG. 2, the spear 2 includes of an outer pipe 20 having a lower, tapering end portion 22, in which there is a central passage 24, and an inner pipe 26, which debouches somewhat above the lower, inwards thickened pipe end portion 22, such that an inner ring slot 28 is formed at this place. At its top, the inner pipe 26 is connected to the conduit 10, while the outer pipe 20 is connected to the conduit 14.

During operation, air will thus be sucked up through the inner pipe 26 as well as be blown down through the outer pipe 20, whereby an air flow will occur at the lower end of the spear as indicated by full line arrows. When the spear 2 is introduced or lowered into a grain material load 30, a sample taking will hereby take place as explained, inasfar as the material, which is led into or up through the lower passage 24, will be successively caught by the air flow and thereby be led to the separator 12, wherefrom the material is separated out in a sample container 32.

The so far described system with associated manner of functioning belongs to the known technique.

In the system according to the invention a small hole 34 is provided at the tip of the spear 2 in the wall of the outer pipe 20, as shown in FIG. 2, or its connecting pipe stub to the hose 14, as shown in FIG. 1. The hole 34 may for that matter be provided anywhere on the pressure side of the blower 16, only in such a manner that it is ensured that a weak air flow is pressed out through this hole. A consequence hereof will be that a correspondingly weak air flow will be sucked into the otherwise closed system wherever possible, i.e. through the lower pipe passage as indicated by a dotted arrow 36, and as mentioned a quite substantial increase of the sampling accuracy is hereby obtained.

It will be appreciated that with the system of the invention a considerable air flow lay circulate through the system so as to give rise to but a very weak and well controlled air intake 36 through the sample intake end 24 of the spear, i.e. the sample material will be rapidly moved away from the intake area entirely independently of the added weak external suction action. In other words, despite an advantageous, powerful pneumatic conveying of the material away from the intake area there is provided for an external suction which is both weak enough to avoid the said "vacuum cleaner effect" and yet strong enough to ensure just a sufficient suction for compensating for the pressure exerted on the grain material and its impurities by the introduction of the spear end into the material.

Figure 3:
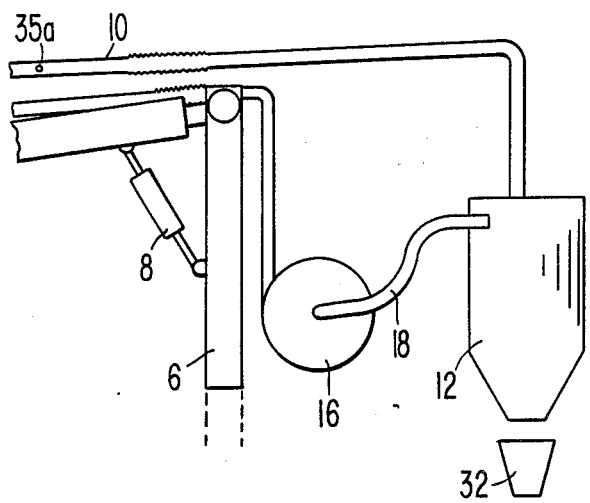
FIG. 3 is a partial schematic view of another embodiment of a sampling system according to the present invention.

All according to the length of the spear, whereby a long spear will present an increased resistance to the introduced air flow and thus condition an increased outflow of air through the hole 34, it may be desirable to reduce the effective vacuum adjacent the spear tip, and it has been found that this is advantageously achievable by providing a still smaller hole 35 in the hose connection as shown in FIG. 1 or a hole 35a in the wall of the suction conduit 10 as shown most clearly in FIG. 3.

Figure 4:
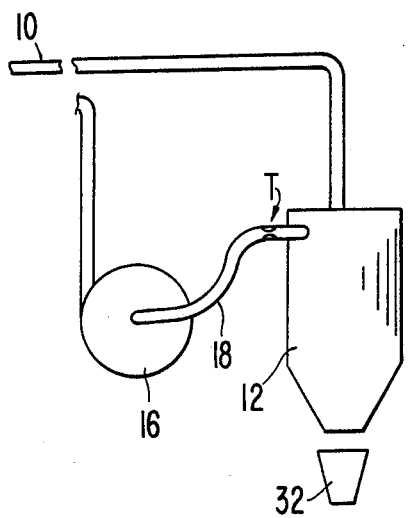
FIG. 4 is a partial schematic view of yet another embodiment of a sampling system according to the present invention.

Thus, what is aimed at is the provision of a well controlled external suction, which should be adjusted to be in the range of 100–250 mm water column, preferably, 150–220 mm. The hole 34 is used for creating the suction, and if required the hole 35 somewhere on the suction side is used for limiting the suction. Such a limitation might be achievable by other means such as, for example, as shown in FIG. 4 wherein a throttling of the blower is accomplished by providing a suitable throttling means generally designated by the reference character T; however, it has been found that the use of the hole 35 is preferable for achieving a high accuracy.

It may be experienced that for different types of material as well as for different lengths of the hose connection 10 it can be necessary to adjust the size of the hole or holes, and though adjustable throttling means could be used it is preferable to arrange for rather large holes and for a series of different nozzle plugs for use therein.

I claim:

1. A sampling system for taking samples from loads of granular material, the sampler system comprising a pipe-shaped sampling spear for introduction or lowering into or down into selected areas of a load of granular material, connection means provided at one end of the sampling spear for connecting the sampling spear with a pressure side of a blower means and, through a sample separator means, with a suction side of the blower means, inlet nozzle means provided at an opposite free end of the sampling spear including an open pipe end, which, internally in the sampling spear is in free connection with a mouth of a central pipe connected to said suction side of the blower means, the free connection comprising an open space axially separating said inlet nozzle means and the mouth of the central pipe, an annular slot in free connection with said open space and occurring between the central pipe and an outer pipe, said annular slot being connected to the pressure side of the blower means through a connection to the outer pipe, and wherein an exhaust hole means, small in cross-sectional area as compared with an internal cross-sectional area of the central pipe, is provided in a wall of one of the outer pipe and connection means between the pressure side of the blower means and the outer pipe of the sampling spear.

2. A system according to claim 1, wherein the cross-sectional area of the exhaust hole means is in a range of 50–200 mm$^2$ for the internal cross-sectional area of the central pipe in a range of 500–1000 mm$^2$.

3. A system according to claim 1, wherein the exhaust hole means is provided near the connection means of the sampling spear.

4. A system according to claim 1, further comprising another hole means of a smaller cross-sectional area than said exhaust hole means, said another hole means being provided in a wall of a suction conduit between the sampling spear and the sample separator means.

5. A system according to one of claims 1 or 4, wherein means are provided for adjusting parameters of the system such that at the free end of the sampling spear a vacuum of 100–250 mm water column is created.

6. A system according to claim 5, wherein a vacuum of 150–220 mm is created.

* * * * *